United States Patent [19]

Lang et al.

[11] Patent Number: 4,585,597
[45] Date of Patent: Apr. 29, 1986

[54] 3-BENZYLIDENE-CAMPHORS, PROCESS FOR THEIR PREPARATION AND THEIR USE IN PROTECTION AGAINST UV RAYS

[75] Inventors: Gerard Lang, Saint Gratien; Madeleine Leduc, Paris; Alain Malaval, Aulnay-sous-Bois, all of France

[73] Assignee: L'Oreal, Paris, France

[21] Appl. No.: 505,090

[22] Filed: Jun. 16, 1983

[30] Foreign Application Priority Data

Jun. 15, 1982 [FR] France ............... 82 10425

[51] Int. Cl.⁴ .................................. C07C 143/52
[52] U.S. Cl. ......................... 260/507 R; 514/510; 514/517
[58] Field of Search ............ 560/51, 507 R; 514/510, 514/517

[56] References Cited

U.S. PATENT DOCUMENTS 3,781,417  12/1973  Welters et al. ............... 424/59

FOREIGN PATENT DOCUMENTS

| | | |
|---|---|---|
| 2199971 | 4/1974 | France . |
| 2236515 | 2/1975 | France . |
| 2282426 | 3/1976 | France . |
| 2383904 | 10/1978 | France . |
| 2402647 | 4/1979 | France . |
| 2421878 | 11/1979 | France . |
| 2430938 | 2/1980 | France . |

OTHER PUBLICATIONS

J. Willis et al, Journal of Investigative Dermatology, vol. 59, No. 6, pp. 416–420 (1973).

*Primary Examiner*—Paul J. Killos
*Attorney, Agent, or Firm*—Fleit, Jacobson, Cohn & Price

[57] ABSTRACT

The invention relates to new 3-benzylidene-camphor derivatives of the formula:

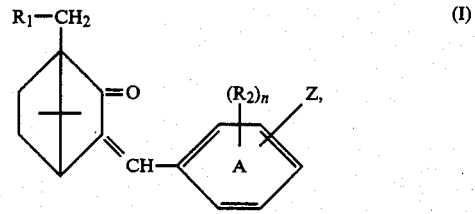

in which $R_1$ denotes H or $SO_3^\ominus M^\oplus$, with M=H, an alkali metal or $N^\oplus(R_3)_4$, with $R_3$=H or $C_1$–$C_4$ alkyl or hydroxyalkyl; $R_2$ denotes $C_1$–$C_4$ alkyl or $C_1$–$C_4$ alkoxy and n=0–4; and Z denotes

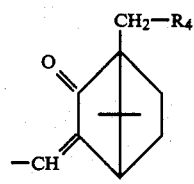

in which $R_4$ has the same meaning as $R_1$ and can be identical or different, or alternatively

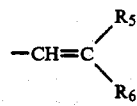

in which $R_5$ denotes H, optionally substituted aryl, $C_1$–$C_4$ alkyl, —CN, —COOR7 or

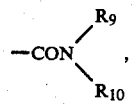

and $R_6$ denotes —COOR8 or

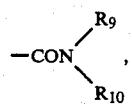

in which $R_7$ and $R_8$, which are identical or different, denote alkyl, alkenyl, cycloalkyl or aralkyl and $R_9$ and $R_{10}$, which are identical or different, denote H, alkyl, alkenyl or cycloalkyl; if $R_5$=H, alkyl or aryl, $R_6$ can represent —COO$^\ominus$M$^\oplus$; the methylidene-camphor radical, on the one hand, and the radical Z, on the other hand, are in the meta or para position. These derivatives act as sun filters.

14 Claims, No Drawings

3-BENZYLIDENE-CAMPHORS, PROCESS FOR THEIR PREPARATION AND THEIR USE IN PROTECTION AGAINST UV RAYS

The present invention relates to compounds derived from 3-benzylidene-camphor, to a process for their preparation and to their use in protection against ultraviolet radiation in the cosmetics field.

It is known that light radiation with wave-lengths of between 280 and 400 nm makes it possible to brown the human epidermis and that rays with wave-lengths of between 280 and 320 nm, known by the name UV-B can also cause erythema and skin burns, which can hinder the development of a tan.

It is already known to use compounds which are active in the abovementioned wavelength range of 280–320 nm. U.S. Pat. No. 3,781,417 describes 3-(4'-methylbenzylidene)-camphor, the absorption maximum of which is at 297 nm, as a UV-B absorber. This compound has good solubility in oils, but is insoluble in water.

Other benzylidene-camphor derivatives are also known for possessing absorption properties in the wave-length range of 280–320 nm. These include benzylidene-camphor derivatives containing a quaternary ammonium radical on the benzene nucleus, in the para position relative to the bornylidene radical, according to French Pat. No. 2,199,971, benzylidene-camphor derivatives sulphonated on the methyl radical in the 10-position of the camphor or in the 3'-position or 4'-position on the benzene nucleus, according to French Pat. Nos. 2,282,426 and 2,236,515, and p-methylbenzylidene-camphor derivatives substituted on the p-methyl group, according to French Pat. Nos. 2,383,904, 2,402,647 and 2,421,878.

However, although the UV-B rays with wavelengths of between 280 to 320 nm play a predominant part in the production of solar erythema and must be filtered out, it is no less true that the UV-A rays, with wavelengths of between 320 and 400 nm, which cause the skin to brown, also damage the skin, in particular in the case of a sensitive skin or a skin continually exposed to solar radiation. It has been found that the UV-A rays can potentiate the action of the UV-B rays, as has been described by several groups of authors and more particularly by J. Willis, A. Kligman and J. Epstein (The Journal of Investigative Dermatology, Volume 59, No. 6, page 416, 1973) under the name Photo-enhancement. The UV-A rays favour the initiation of the erythematous reaction or increase this reaction in certain subjects. Likewise, they can be the cause of phototoxic or photoallergic reactions.

Attempts have therefore been made to find compounds which absorb the UV rays strongly over a wide band; and compound absorbing the UV rays with wavelengths of between 315 and 340 nm, in particular, have been discovered, such as 3-para-hydroxybenzylidene-bornan-2-ones of French patent application No. 2,430,938 or 3-cinnamylidene-camphor of U.S. Pat. No. 3,781,417.

Furthermore, it is known that the constituents present in cosmetic preparations, and in particular certain dyestuffs in dyeing compositions, coloured hair lacquers, shampoos, setting lotions and make-up products such as tinted creams, nail varnishes and lipsticks, do not always possess sufficient light stability, and that they degrade under the action of light radiation.

Consequently, it is desirable to have available a group of compounds capable of absorbing both the UV-A rays and the UV-B rays, and to be able to protect the various products sensitive to this radiation by incorporating such agents which filter out the UV-A and UV-B rays into the products, preparations and compositions sensitive to this radiation.

We have discovered that, surprisingly, certain 3-benzylidene-camphor derivatives have good filtering properties with respect to UV-A and UV-B rays, are soluble in the customary cosmetic solvents and have good heat stability and excellent photochemical stability.

The present invention therefore provides 3-benzylidene-camphors of the general formula:

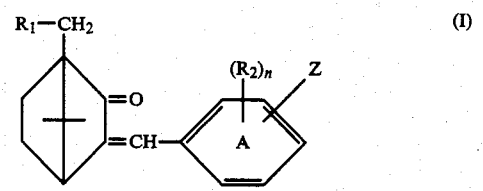 (I)

in which $R_1$ denotes a hydrogen atom or a radical $-SO_3^-M^+$, in which M denotes a hydrogen atom, an alkali metal or a group $N(R_3)_4^+$, $R_3$ denoting a hydrogen atom or a $C_1$ to $C_4$ alkyl or hydroxyalkyl radical, $R_2$ denotes a linear or branched $C_1$ to $C_4$ alkyl radical or a $C_1$ to $C_4$ alkoxy radical, n being 0 or an integer from 1 to 4; and when n is 2 or more $R_2$ radicals can be the same or different; and Z represents a group

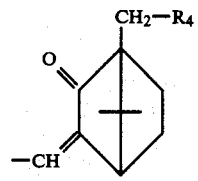

in which $R_4$ has the same meanings as $R_1$ and can be identical to $R_1$ or different from $R_1$, or alternatively a group

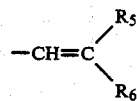

in which $R_5$ denotes a hydrogen atom, a $C_1$ to $C_4$ alkyl radical, an aryl radical optionally substituted by one or more halogen atoms or by $C_1$ to $C_4$ alkyl or alkoxy groups, or a radical $-CN$, $-COOR_7$ or

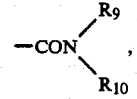

and $R_6$ denotes a group $-COOR_8$ or

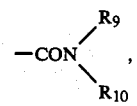

$R_7$ and $R_8$, which are identical or different, being alkyl, alkenyl, cycloalkyl or aralkyl radicals containing up to 20 carbon atoms, which are optionally substituted by one or more hydroxyl, alkoxy, amine or quaternary ammonium groups, and $R_9$ and $R_{10}$, which are identical or different, denoting a hydrogen atom or alkyl, alkenyl, cycloalkyl or aralkyl radicals containing up to 20 carbon atoms, which are optionally substituted by one or more hydroxyl, alkoxy, amine or quarternary ammonium groups, or alternatively, if $R_5$ denotes a hydrogen atom, an alkyl radical or an optionally substituted aryl radical, $R_6$ can also represent a radical —COO$^\ominus$M$^\oplus$, M being defined as above, the methylidene-camphor radical, on the one hand, and the radical Z, on the other hand, being attached to the aromatic nucleus A either in the meta position or in the para position relative to one another.

The following radicals may be mentioned amongst the preferred radicals $R_7$, $R_8$, $R_9$ and $R_{10}$: ethyl, propyl, butyl, hexyl, 2-ethylhexyl, menthyl, oleyl, benzyl and 4-methoxybenzyl, and the phenyl radical may be mentioned amongst the preferred aryl radicals for $R_5$.

Depending on the nature of the substituents $R_1$, $R_2$, $R_4$, $R_5$ and $R_6$, the compounds of the formula (I) can be water-soluble or liposoluble.

If Z represents a group

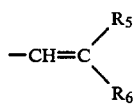

and if $R_6$ is different from —COO$^\ominus$M$^\oplus$, $R_1$ is preferably a hydrogen atom; these compounds are generally lipophilic.

The compounds of the formula (I) have molar absorption coefficients ($\epsilon$) which are generally high, generally above 30,000 at between 300 and 380 nm.

The position of the absorption maxima for the compounds of the formula (I) depends on the nature of $R_2$ and also on the relative position of the methylidene-camphor radical, and the radical Z to one another and also to the group(s) $R_2$ when the latter are electron donors.

In general, the products in which the methylidene-camphor radical and the radical Z are in the para position absorb at wavelengths higher than those at which the corresponding meta-substituted products absorb.

According to the invention, a wide range of compounds is therefore available, constituting sun filters which filter out both the UV-A rays and the UV-B rays.

The present invention also provides a process for the preparation of the compounds of the formula (I).

The compounds of the formula (I) can be obtained by the following processes, which differ according to whether the compounds are symmetrical or asymmetrical.

1 - Process for the preparation of the symmetrical compounds of the formula (I)

in which

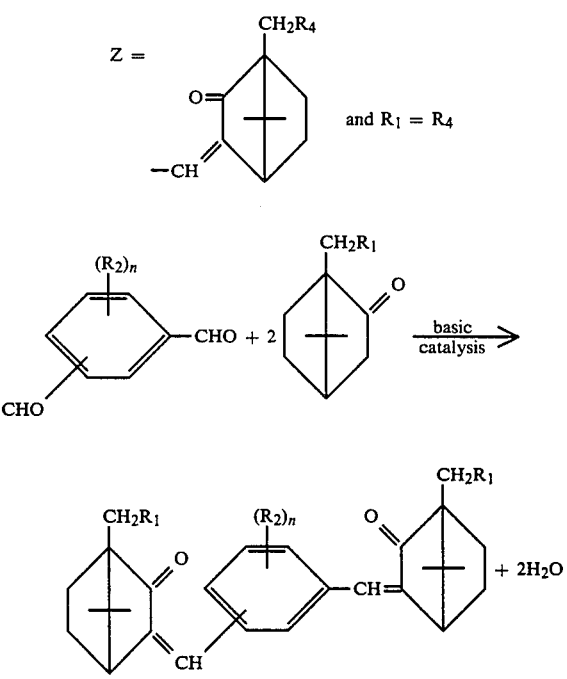

This type of reaction can be carried out in an anhydrous solvent, which is preferably aprotic, in the presence of an organic base such as an alkali metal alcoholate, or of a inorganic base such as an alkali metal amide or hydride, the water formed being removed. In certain cases, it is also possible to carry out the reaction in a water-immiscible solvent, in the presence of aqueous solutions of sodium hydroxide or potassium hydroxide.

2 - General process for the preparation of the symmetrical and asymmetrical compounds (a) Z=

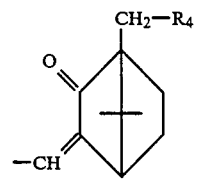

$R_4$ being identical to $R_1$ or different from $R_1$.

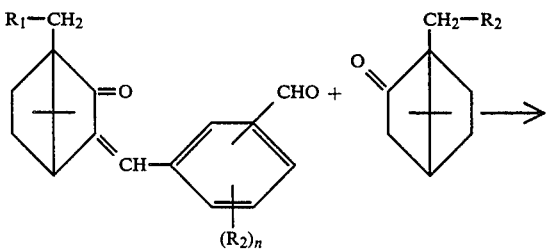

-continued

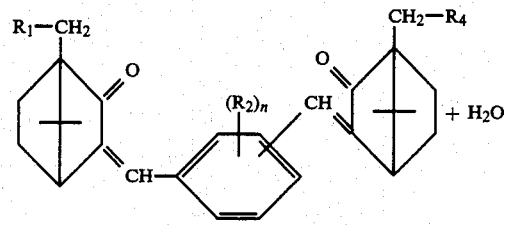

The reaction can be carried out under conditions identical to those described for process (1). (b) Z=

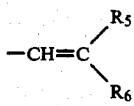

The reaction scheme used is as follows:

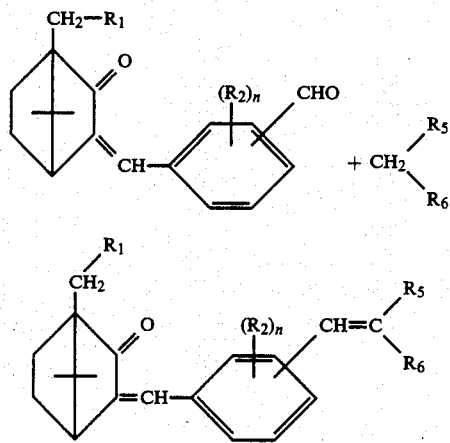

It corresponds to the conventional formation of a cinnamic acid derivative from an aromatic aldehyde.

The preferred compounds (I) according to the invention are the compounds in which Z is in the para position, the majority of which constitute sun filters which filter out the UV-A radiation, that is to say filters having an absorption maximum above or equal to 320 nm.

These compounds desirably have the formula:

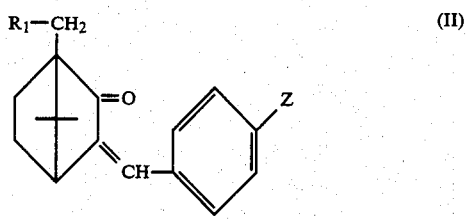
(II)

The compounds of the formula (II) in which Z is in the para position) have very good solubility in water or oils, depending on the nature of the substituents.

Of course, the compounds of the formula (I) or (II) can give rise to "cis-trans" isomerism around one or more double bonds, and all the isomers form part of the present invention.

The compounds of the formula (I) or (II) according to the invention are further illustrated by Examples (1) to (23) which follow, and the characteristics of these compounds: preparative procedure, melting point, wavelength corresponding to the absorption maximum $(\kappa)_{max}$, molar absorption coefficient ($\epsilon$) and analysis, are indicated in the table below.

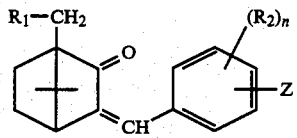

| Example | $R_1$ | n, $R_2$ | Z | Preparative procedure | Melting point | UV absorption $\lambda$max. ($\epsilon$) | Analysis |
|---|---|---|---|---|---|---|---|
| 1 | H | 0 | —CH⟨ ⌬ —CH₂SO₃H in the para position | A | 258° C. | 347 nm (CHCl₃) ($\epsilon = 35,000$) | Theory: C: 69.68 H: 7.10 S: 6.64 Found: C: 69.86 H: 7.07 S: 6.59 |
| 2 | H | 0 | —CH⟨ ⌬ —CH₂SO₃⊖N⊕H(CH₂CH₂OH)₃ in the para position | A | — | 342 nm (CHCl₃) ($\epsilon = 39,600$) | — |
| 3 | H | 0 | —CH=C(CO₂—2-ethylhexyl)(CO₂—2-ethylhexyl) in the para position | C | oil | 328 nm (EtOH) ($\epsilon = 39,000$) | Theory: C: 76.77 H: 9.40 Found: C: 76.76 H: 9.34 |

-continued

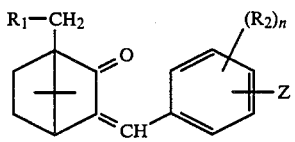

| Example | $R_1$ | n, $R_2$ | Z | Preparative procedure | Melting point | UV absorption $\lambda$max. ($\epsilon$) | Analysis |
|---|---|---|---|---|---|---|---|
| 4 | H | 0 | —CH=CH(H)(CO$_2$H) in the para position | B | 227° C. | 327 nm (EtOH) ($\epsilon$ = 41,000) | Acid number: Theory: 3.22 meq/g Found: 3.28 meq/g |
| 5 | H | 0 | —CH=CH(H)(CO$_2$ethyl) in the para position | D | 132° C. | 350 nm (CHCl$_3$) ($\epsilon$ = 50,000) | Theory: C: 76.01 H: 6.93 N: 3.85 Found: C: 75.98 H: 6.88 N: 3.73 |
| 6 | H | 0 | —CH= (cyclohexanone ring) in the para position | A | 234° C. | 337 nm (CHCl$_3$) ($\epsilon$ = 38,700) | Theory: C: 83.54 H: 8.51 O: 7.95 Found: C: 83.54 H: 8.56 O: 7.91 |
| 7 | H | 0 | —CH=C(CO$_2$ethyl)(CO$_2$ethyl) in the para position | C | 84° C. | 335 nm (CHCl$_3$) ($\epsilon$ = 39,500) | Theory: C: 73.15 H: 7.37 Found: C: 73.06 H: 7.30 |
| 8 | H | 0 | —CH=CH—CO$_2$—(CH$_2$)$_3$CH$_3$ in the para position | B + E | 80° C. | 331 nm (CHCl$_3$) ($\epsilon$ = 43,500) | Theory: C: 78.65 H: 8.25 Found: C: 78.75 H: 8.24 |
| 9 | H | 0 | —CH=C(CN)(CO$_2$—2-ethylhexyl) in the para position | D | 83° C. | 355 nm (CHCl$_3$) ($\epsilon$ = 39,000) | Theory: C: 77.82 H: 8.33 N: 3.13 Found: C: 77.83 H: 8.28 N: 3.12 |
| 10 | H | n = 4 $R_2$ = CH$_3$ | —CH= (cyclohexanone ring) in the para position | F | 270° C. | 290 nm (CHCl$_3$) ($\epsilon$ = 12,500) | Theory: C: 83.79 H: 9.23 Found: C: 83.59 H: 9.24 |
| 11 | H | 0 | —CH=C(CO$_2$—menthyl)(CO$_2$—menthyl) in the para position | C | <55° C. | 332 nm (CHCl$_3$) ($\epsilon$ = 39,000) | Theory: C: 78.05 H: 9.27 Found: C: 78.01 H: 9.29 |
| 12 | H | 0 | —CH=CH—CONH—2-ethylhexyl in the para position | B + G + H | <55° C. | 328 nm (CHCl$_3$) ($\epsilon$ = 47,000) | Theory: C: 79.76 H: 9.32 N: 3.32 Found: C: 79.69 H: 9.35 N: 3.25 |
| 13 | H | 0 | —CH=CH—CO$_2$—CH$_2$—⟨ ⟩—OCH$_3$ in the para position | B + G + I | 144° C. | 328 nm (CHCl$_3$) ($\epsilon$ = 47,800) | Theory: C: 78.11 H: 7.02 Found: C: 78.35 H: 7.06 |
| 14 | H | 0 | —CH= (cyclohexanone ring) in the meta position | J | 152° C. | 295 nm (CHCl$_3$) ($\epsilon$ = 41,500) | Theory: C: 83.54 H: 8.51 Found: C: 83.48 H: 8.50 |

-continued

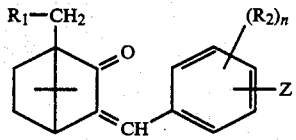

| Example | $R_1$ | n, $R_2$ | Z | Preparative procedure | Melting point | UV absorption $\lambda$max. ($\epsilon$) | Analysis |
|---|---|---|---|---|---|---|---|
| 15 | H | 0 | —CH=CH—COO(CH$_2$)$_8$—CH=CH—(CH$_2$)$_7$—CH$_3$ in the para position | B + K | oil | 329 nm (EtOH) ($\epsilon$ = 36,100) | Theory: C: 81.38 H: 10.06 Found: C: 81.16 H: 10.19 |
| 16 | H | 0 | —CH= [camphor with CH$_2$SO$_3$H] in the meta position | A | Softening point 134° C. | 298 nm (water) ($\epsilon$ = 37,000) | Acid number: Theory: 2.07 meq/g Found: 1.98 meq/g |
| 17 | H | 0 | —CH=C(CO$_2$H)(phenyl) in the para position | L | 238° C. | 334 nm (EtOH) ($\epsilon$ = 32,750) | Acid number: Theory: 2.59 meq/g Found: 2.56 meq/g |
| 18 | H | 0 | —CH=C(CO$_2$C$_6$H$_{13}$)(phenyl) in the para position | L + M | 86° C. | 335 nm (EtOH) ($\epsilon$ = 40,000) | Theory: C: 81.66 H: 8.14 Found: C: 81.34 H: 8.27 |
| 19 | —SO$_3$H | 0 | —CH= [camphor with CH$_2$SO$_3$H] in the para position | N | 255° C. with decomposition | 342 nm (H$_2$O) ($\epsilon$ = 42,300) | Theory: C: 56.18 H: 6.35 O: 26.76 S: 10.70 Found: C: 55.92 H: 6.40 O: 26.17 S: 10.88 |
| 20 | —$^\ominus$SO$_3$Na$^\oplus$ | 0 | —CH= [camphor with CH$_2$SO$_3^\ominus$Na$^\oplus$] in the para position | N | — | 345 nm (H$_2$O) ($\epsilon$ = 44,000) | — |
| 21 | $m$SO$_3^\ominus$ NH(CH$_2$CH$_2$OH)$_3$ | 0 | —CH= [camphor with CH$_2$SO$_3$N$^\oplus$H(CH$_2$CH$_2$OH)$_3$] in the para position | N | — | 345 nm (H$_2$O) ($\epsilon$ = 40,000) | — |
| 22 | H | 0 | —CH=C(CO$_2$ethyl)(CH$_3$) in the para position | O | 106° C. | 323 nm (EtOH) ($\epsilon$ = 37,360) | Theory: C: 78.37 H: 8.01 Found: C: 78.35 H: 8.02 |
| 23 | H | 0 | —CH=CH—CO$_2$ethyl in the meta position | P | 85.5° C. | 283 nm (EtOH) ($\epsilon$ = 45,300) | Theory: C: 78.07 H: 7.74 Found: C: 78.04 H: 7.72 |

The procedures (A) to (P) used to prepare the compounds (1) to (23) are set out below.

PROCEDURE A 134 g of 4'-formyl-3-benzylidene-camphor, 1,350 ml of dry toluene, 116 g of camphosulphonic acid and 22 g of sodium hydroxide pellets are placed in an equipped 3 liter three-necked round-bottomed flask. The mixture is heated under reflux for 1 hour, the water formed being separated off with the aid of a Dean-Stark apparatus (18 ml). The solution is cooled and poured into 3 liters of isopropyl ether. The precipitate is filtered off, washed with isopropyl ether and dried.

The compound obtained is dissolved in 2 liters of hot acetone and the solution is acidified with 25 ml of concentrated hydrochloric acid. The inorganic salts which precipitate are filtered off and the filtrate is evaporated to dryness. The residue is taken up in 1 liter of isopropyl ether, filtered off and dried in vacuo. This gives 191 g of compound (1) (yield=79%).

Compound (2) is obtained by neutralising an aqueous solution of compound (1) with triethanolamine used stoichiometric proportions. The aqueous solution is lyophilised to remove the water and to give the compound in powder form.

Procedure A is also used to prepare compound (6), the camphosulphonic acid being replaced by camphor, and to prepare compound (16), the 4'-formyl-3-benzylidene-camphor being replaced by 3'-formuyl-3-benzylidene-camphor.

PROCEDURE B 22 g of malonic acid and 40 ml of dry pyridine are placed in an equipped 250 ml round-bottomed flask. The mixture is stirred until dissolution is complete. 1 ml of piperidine is then added, followed by 27 g of 4'-formyl-3-benzylidene-camphor, and the whole is heated gradually to 110° C. Gas is evolved and this stops after a heating time of about 1 hour 30 minutes.

The solution is then cooled and acidified by adding 100 ml of 6 N hydrochloric acid. The precipitate formed is filtered off, washed with water until the washings are neutral, and dried in vacuo.

This gives 30 g of compound (4) (yield=96%).

PROCEDURE C 69 g of 2-ethylhexyl malonate, 2 ml of piperidine, 500 ml of ethanol and 54 g of 4'-formyl-3-benzylidene-camphor are placed in an equipped 1 liter round-bottomed flask.

The mixture is heated under reflux for 24 hours. A further 2 ml of piperidine are then added and the mixture is heated under reflux for 6 hours.

The solution is cooled and concentrated in vacuo. The residue is taken up in 500 ml of toluene. The organic phase is washed several times with water, dried and concentrated in vacuo.

The oil obtained is chromatographed on silica (eluant: acetone/hexane (1/9)).

This gives 55 g of compound (3) (yield: 47%).

To prepare compounds (7) and (11), the 2-ethylhexyl malonate is replaced by ethyl malonate and menthyl malonate respectively.

PROCEDURE D 10.6 ml of ethyl cyanoacetate, 50 ml of absolute ethanol and 1.5 g of potassium fluoride, as a catalyst, are placed in an equipped 250 ml round-bottomed flask.

27 g of 4'-formyl-3-benzylidene-camphor are added to this mixture in small portions. The reaction mixture becomes pasty, 125 ml of absolute ethanol are then introduced and the mixture is stirred at 50° C. for 1 hour.

The mixture is cooled and the precipitate is filtered off, washed with 200 ml of ethanol and then with 200 ml of water and finally dried in vacuo.

This gives 32.7 g of compound (5) (yield: 90%).

To obtain compound (9), the ethyl cyanoacetate is replaced by 2'-ethylhexyl cyanoacetate.

PROCEDURE E 56 g of p-(2-oxo-3-bornylidene-methyl)-cinnamic acid (compound 4), 27 g of butanol, 800 ml of dry benzene and 4 ml of concentrated sulphuric acid are placed in an equipped 2 liter reactor.

The mixture is heated under reflux for 4 hours, the water formed being separated off with the aid of a Dean-Stark apparatus.

The solution is then cooled and subsequently washed with water, dried and evaporated to dryness.

The residue is recrystallised from ethanol.

This gives 70 g of compound (8) (yield=76%).

PROCEDURE F 40 g of camphor, 200 ml of dry toluene, 23 g of tetramethylterephthaldehyde and 9.6 g of sodium hydroxide pellets are placed in an equipped 1 liter reactor.

The mixture is heated under reflux for 96 hours, the water formed being separated off.

The organic phase is then washed with water, dried and concentrated in vacuo.

The residue is taken up in 500 ml of toluene and filtered off on silica. The solution is evaporated to dryness. This gives 21 g of compound (10) (yield=38%).

PROCEDURE G 31 g of p-(2-oxo-3-bornylidene-methyl)-cinnamic acid (compound 4), 200 ml of dry toluene and 24 g of thionyl chloride are placed in an equipped 500 ml reactor.

The mixture is heated under reflux for 2 hours. The excess thionyl chloride is driven off and the toluene is then distilled in vacuo.

The residue is recrystallised from a 40/60 toluene/hexane mixture.

After drying, 26 g of p-(2-oxo-3-bornylidene-methyl)-cinnamoyl chloride are obtained (yield=80%).

PROCEDURE H 10 g of the acid chloride obtained under G, 3.9 g of 2-ethylhexylamine, 4.2 ml of triethylamine and 100 ml of methylene chloride are placed in an equipped 250 ml round-bottomed flask.

The mixture is heated under reflux for 2 hours. After cooling, the organic phase is washed with water, dried and filtered and the filtrate is concentrated to dryness.

The oily residue is dried in vacuo to give an amorphous solid.

This gives 12.2 g of compound (12) (yield=96%).

PROCEDURE I 4.15 g of p-methoxybenzyl alcohol and 20 ml of pyridine are placed in an equipped 100 ml round-bottomed flask, and 9.9 g of the acid chloride obtained under G are introduced in small portions at ambient temperature.

The reaction is slightly exothermic.

When the addition has ended, the mixture is heated at 70° C. for 1 hour.

After cooling, the solution is poured into a mixture of 200 ml of ice and 30 ml of concentrated hydrochloric acid.

The precipitate formed is filtered off, washed with water and recrystallised from acetone. This gives 6.8 g of compound (13) (yield=52%).

PROCEDURE J 25 g of potassium tert.-butylate and 250 ml of toluene are placed in an equipped one liter reactor, and 33.5 g of camphor are then introduced in small portions.

The reaction is exothermic (maximum temperature 60° C.).

After the mixture has cooled to 40° C., a solution of 13.4 g of isophthaldehyde in 200 ml of dry toluene is introduced dropwise.

The mixture is then heated under reflux for about 4 hours and subsequently poured into 700 ml of ice containing 25 ml of concentrated hydrochloric acid. The solid formed is filtered off (isophthalic acid) and the filtrate is left to separate.

The organic phase is separated off, dried and concentrated in vacuo. The oily residue is chromatographed on a silica column (eluant=methylene chloride). This gives 10 g of compound (14).

PROCEDURE K 300 ml of dry benzene, 200 ml of dry toluene, 228 g of oleyl alcohol, 3.2 ml of concentrated sulphuric acid and then 45 g of p-(2-oxo-3-bornylidene-methyl)-cinnamic acid (compound 4) are placed in an equipped 2 liter reactor.

The mixture is heated under reflux for 5 hours, the water formed being separated off with the aid of a Dean-Stark apparatus.

The solution is then cooled and is subsequently washed with water, dried and evaporated to dryness. The residue is subjected to distillation under 0.1 mm Hg at 160°-174° C. in order to remove the excess oleyl alcohol. The expected ester is isolated by column chromatography in the presence of silica gel and chloroform (10 liters of $CHCl_3$ + 2 kg of silica gel).

The chloroform part, containing the oleyl p-(2-oxo-3-bornylidene-methyl)-cinnamate, is concentrated to give 40 g of compound (15) (yield=40%).

PROCEDURE L

A mixture containing 17.4 g (0.1 mol) of potassium phenylacetate, 5 g (0.035 mol) of potassium carbonate, 0.5 ml of pyridine, 26.8 g (0.1 mol) of 4'-formyl-3-benzylidene-camphor and 15.3 g (0.15 mol) of acetic anhydride is heated for 2 hours at 180°-190° C. A stream of nitrogen is maintained throughout the heating period.

After cooling, 300 ml of ice then 50 ml of 6 N potassium hydroxide solution are added. Extraction is carried out with 50 ml of ether and the aqueous phase is then acidified. The precipitate is recrystallised from 100 ml of 50% strength ethyl alcohol. This gives 15.2 g of compound (17).

PROCEDURE M

A solution of 7.72 g (0.02 mol) of compound (17) obtained by procedure L, 5 ml of hexanol, 50 ml of toluene and 3 drops of concentrated sulphuric acid is heated under reflux in a round-bottomed flask equipped with a Dean-Stark apparatus.

After 3 hours under reflux, the reaction mixture is concentrated. The residue is recrystallised from ethanol. This gives 5.9 g of pale yellow product (18).

PROCEDURE N 223 g (2 mols) of 97% strength sodium methylate are added to a suspension of 464.8 g (2 mols) of 10-d,l-camphosulphonic acid in 4 liters of toluene and 0.2 liter of methanol, and the mixture is then heated under reflux for 30 minutes.

A solution of 134.2 g (1 mol) of terephthalaldehyde in 1 liter of a 90/10 toluene/methanol mixture is then added in the course of 2 hours, under nitrogen. The mixture is kept under reflux for 1 hour and then cooled to ambient termperature.

The toluene is drawn off and the product is taken up in 1.5 liters of water and 1.5 liters of 35% strength hydrochloric acid. The mixture is heated under reflux for 1 hour, the residual toluene being distilled.

After the medium has been concentrated and cooled, the concentrate is filtered and the material on the filter is washed with 6 N hydrochloric acid and dried in vacuo at 80° C. and then at 100° C. This gives 395 g of compound (19).

This is dissolved in water, the stoichiometric amount of sodium carbonate is added and the sodium disulphonate, which precipitates, is easily obtained. After dilution with acetone, filtration and drying in vacuo at 80° C. and then at 100° C., the sodium disulphonate (20) is obtained with a virtually quantitative yield.

The triethanolamine salt (21) is obtained in the same way from compound (19) by using a stoichiometric amount of triethanolamine.

PROCEDURE O 5 ml ($10^{-2}$ mol) of ethyl 2-diethylphosphonopropionate, 5.4 g of 4'-formyl-3-benzylidene-camphor $2.10^{-2}$ mol), 40 ml of a saturated solution of potassium carbonate and 40 ml of water are introduced into a 250 ml round-bottomed flask. After vigorous stirring for 24 hours at ambient temperature, extraction is carried out with 3 times 50 ml of toluene. The organic phase is washed with water, distilled, dried and then evaporated to give 8 g of a yellowish oil, which crystallises in the cold. The product is recrystallised from hexane, which gives 5.2 g of white crystals of compound (22).

PROCEDURE P

A suspension of 1 g of powdered potassium hydroxide in 30 ml of dioxane is placed in a 100 ml round-bottomed flask. A solution of 1.12 g ($5.10^{-3}$ mol) of ethyl diethylphosphonoacetate and 1.34 g of 3'-formyl-3-benzylidene-camphor ($5.10^{-3}$ mol) in 30 ml of dioxane is added dropwise. After stirring for 1 hour, the reaction medium is diluted with 40 ml of toluene. Filtration and evaporation of the solvents gives an oil, which crystallises in the cold. After recrystallisation from haxane, a product which melts at 85.5° C. (23) is obtained.

The present invention also provides a cosmetic composition containing at least one 3-benzylidene-camphor derivative of the formula (I) according to the invention, as an agent for protection against ultraviolet rays, in a cosmetically acceptable medium.

If it is used as a composition intended for protecting the human epidermis against ultraviolet rays, the cosmetic composition according to the invention can be presented in the widest variety of forms normally used for this type of composition. It can be, in particular, in the form of a solution, a lotion, an emulsion such as a cream or a milk, an aqueous-alcoholic or alcoholic gel or a solid stick, or can be packaged in an aerosol.

It can contain the cosmetic adjuvants normally used in this type of composition, such as thickeners, softeners, humectants, superfatting agents, emollients, wetting agents, surface-active agents, preservatives, anti-foam agents, perfumes, oils, waxes, dyestuffs and/or pigments serving to colour the composition itself or the skin, bactericides or any other ingredient normally used in cosmetics.

The compound of the formula (I) is suitably present in proportions by weight of 0.5 to 15%, relative to the total weight of the composition.

Solubilisation solvents which can be used include a lower monoalcohol or polyol or a mixture thereof, or an aqueous-alcoholic solution. The particularly preferred monoalcohols or polyols are ethanol, isopropanol, propylene glycol and glycerol.

One embodiment of the invention is an emulsion in the form of a protective cream or milk comprising, in addition to a compound of the formula (I), at least one fatty alcohol, oxyethyleneated fatty alcohol or fatty acid ester, and, in particular, a fatty acid triglyceride, a fatty acid, lanoline, a natural or synthetic oil, or a wax, in the presence of water.

Another embodiment consists of lotions such as oily-slcoholic lotions based on a lower alcohol such as ethanol, or on a glycol such as propylene glycol, and/or on a polyol such as glycerol, and on a fatty acid ester such as a fatty acid triglyceride.

The cosmetic composition of the invention can also be an aqueous-alcoholic gel comprising one or more lower alcohols such as ethanol, propylene glycol or glycerol, and a thickener, in the presence of water.

The present invention also provides antisunburn cosmetic compositions containing at least one compound of the formula (I), which can be associated with other sun filters specific for UV-B radiation and/or UV-A radiation, which are compatible with the compounds according to the invention. It is thus possible to obtain a formulation which filters out all the UV-B and UV-A radiation.

The compounds according to the invention can be associated with UV-B filters which can be liposoluble compounds or oils having filtering properties, in particular coffee bean oil. Lipophilic UV-B sun filters which may be mentioned include salicyclic acid derivatives such as 2-ethylhexyl salicylate and homomenthyl salicylate, cinnamic acid derivatives such as 2-ethylhexyl p-methoxy-cinnamate and 2-ethoxyethyl p-methoxycinnamate, p-aminobenzoic acid derivatives such as amyl p-aminobenzoate and 2-ethylhexyl p-dimethylaminobenzoate, benzophenone derivatives such as 2-hydroxy-2-methoxybenzophenone and 2,2'-dihydroxy-4-methoxy-benzophenone, and camphor derivatives such as 3-(4-methylbenzylidene)-camphor, optionally associated with 4-isopropyldibenzoylmethane or 3-benzylidene-camphor.

As water-soluble sun filters which filter out the UV-B rays and which can also be associated with the liposoluble or water-soluble filters of the invention, provided that they are compatible with the latter, there may be mentioned the benzylidene-camphor derivatives described in French Pat. Nos. 2,199,971, 2,236,515, 2,383,904, and, more particularly, 4-(2-oxo-3-bornylidene-methyl)-phenyltrimethylammonium methylsulphate and salts of 4-(2-oxo-3-bornylidene-methyl)-benzenesulphonic acid, of 2-methyl-5-(2-oxo-3-bornylidene-methyl)-benzenesulphonic acid and of 2-phenyl-benzimidazole-5-sulphonic acid.

The compounds according to the invention can also be associated with UV-A filters, amongst which dibenzoylmethane derivatives may be mentioned.

It is to be understood that the list of sun filters which can be used in association with the compounds (I) according to the invention is not exhaustive.

The anti-sunburn compositions according to the invention can be presented in the form of, for example, solutions, lotions, emulsions such as a cream or a milk, oils, fatty gels or aqueous-alcoholic or alcoholic gels, or can be packaged in an aerosol or as solid sticks. They can contain the abovementioned cosmetic adjuvants normally used in this type of composition.

The present invention also provides coloured or non-coloured cosmetic compositions containing at least one compound of the formula (I) as an agent for protection against ultraviolet rays.

These compositions may be in the form of, for example, hair composition such as hair lacquers, setting lotions, which optionally have a treating or disentangling function, shampoos, colouring shampoos and hair dyeing compositions, make-up products such as nail varnishes, epidermis treatment creams, make-up foundations and lipsticks, and any other cosmetic composition which, by virtue of its constituents, can present problems of light stability during storage.

The invention also provides a process for protecting the human epidermis against UV-A rays and UV-B rays, which consists in applying, to the skin, at least one compound of the formula (I) in a cosmetically acceptable medium and optionally associated with other agents which absorb UV-A and/or UV-B rays.

The invention also provides a process for protecting coloured cosmetic compositions against UV-A and UV-B rays, which consists in incorporating at least one compound of the formula (I) into these compositions.

The present invention is further illustrated by the following application Examples.

EXAMPLE 24

| Protecting day cream | |
|---|---|
| Compound of Example 7 | 1 g |
| Polyoxyethyleneated fatty alcohols | 7 g |
| Fatty acid triglycerides | 30 g |
| Glycerol monostearate | 2 g |
| Silicone oil | 1.5 g |
| Cetyl alcohol | 1.5 g |
| Preservatives | 0.3 g |
| Perfume | 0.6 g |
| Demineralised water q.s.p. | 100 g |

To prepare this cream, the fatty substances are heated to about 80°–85° C.; the filter of the formula (I) is added. The water is heated separately to 80°–85° C. and the fatty phase is added to the aqueous phase with vigorous stirring; the stirring is maintained for 10 to 15 minutes and the mixture is then left to cool, with moderate stirring, and the perfume is added at about 40° C.

EXAMPLE 25

| Protecting day cream | |
|---|---|
| Compound of Example 6 | 0.5 g |
| Benzylidene-camphor | 0.5 g |
| Triglycerides of $C_8$ to $C_{12}$ fatty acids | 31 g |
| Glycerol monostearate | 6 g |
| Stearic acid | 2 g |
| Cetyl alcohol | 1.2 g |
| Lanoline | 4 g |
| Preservatives | 0.3 g |
| Propanediol | 2 g |
| Triethanolamine | 0.5 g |

-continued

| Protecting day cream | |
|---|---|
| Perfume | 0.5 g |
| Demineralised water q.s.p. | 100 g |

The fatty substances are heated to about 80°–85° C. and the filters are added; with vigorous stirring, the fatty phase is added to the water (containing the water-soluble compounds) heated to about 80°–85° C. beforehand. After vigorous stirring for 15 minutes, the mixture is left to cool, with moderate stirring.

EXAMPLE 26

Day cream

This composition is identical to that of Example b 25, the compound of Example 6 being replaced by 0.8 g of the compound of Example 10.

EXAMPLE 27

| Protecting milk | |
|---|---|
| Compound of Example 8 | 0.5 g |
| Octyl p-dimethylaminobenzoate | 0.5 g |
| Cetyl-stearyl alcohol | 2 g |
| Cetyl alcohol | 2 g |
| Triglycerides of $C_8$ to $C_{12}$ fatty acids | 20 g |
| Lanoline | 4 g |
| Stearic acid | 0.5 g |
| Preservatives | 0.3 g |
| Carbopol 934 (crosslinked polyacrylic acid sold by GOODRICH CHEMICAL) | 0.15 g |
| Triethanolamine | 0.2 g |
| Perfume | 0.4 g |
| Demineralised water q.s.p. | 100 g |

The emulsion is prepared in the same way as in Example 25.

EXAMPLE 28

| Oily-alcoholic sun lotion | |
|---|---|
| Compound of Example 13 | 1.5 g |
| Perfume | 0.5 g |
| 96° strength ethanol | 47.5 g |
| Triglycerides of $C_8$ to $C_{12}$ fatty acids q.s.p. | 100 g |
| 2-Ethylhexyl p-methoxycinnamate | 2 g |

The mixture of the various constituents is heated to about 40°–45° C. in order to homogenise them and give a clear lotion.

EXAMPLE 29

| Sun cream | |
|---|---|
| Compound of Example 8 | 3 g |
| 4-[(2-Oxo-3-bornylidene)-methyl]-phenyl-trimethylammonium methylsulphate | 2.5 g |
| Polyoxyethyleneated fatty alcohols | 7 g |
| Triglycerides of $C_8$–$C_{12}$ fatty acids | 30 g |
| Glycerol monostearate | 2 g |
| Silicone oil | 1.5 g |
| Cetyl alcohol | 1.5 g |
| Preservatives | 0.3 g |
| Perfume | 0.6 g |
| Demineralised water q.s.p. | 100 g |

The preparation of this cream is similar to that of Example 24; in this case, the 4-[(2-oxo-3-bornylidene)-methyl]-phenyltrimethylammonium methylsulphate is dissolved in the water.

EXAMPLE 30

| Sun cream | |
|---|---|
| Compound of Example 7 | 2.5 g |
| Benzylidene-camphor | 4 g |
| Triglycerides of $C_8$ to $C_{12}$ fatty acids | 31 g |
| Glycerol monostearate | 6 g |
| Stearic acid | 2 g |
| Cetyl alcohol | 1.2 g |
| Lanoline | 4 g |
| Preservatives | 0.3 g |
| Propanediol | 2 g |
| Triethanolamine | 0.5 g |
| Perfume | 0.4 g |
| Demineralised water q.s.p. | 100 g |

The filters are dissolved in the fatty phase. The compound of Example 7 can be replaced by 2.5 g of the compound of Example 11.

EXAMPLE 31

| Sun oil | |
|---|---|
| The following ingredients are mixed, if necessary with heating to 40–45° C. to homogenise them: | |
| Compound of Example 8 | 3 g |
| Octyl p-dimethylaminobenzoate | 3 g |
| Cacao butter | 2.5 g |
| Antioxidants | 0.05 g |
| Perfume | 0.5 g |
| Triglycerides of $C_8$ to $C_{12}$ fatty acids q.s.p. | 100 g |

The compound of Example 8 can be replaced by 3 g of the compound of Example 9.

EXAMPLE 32

| Sun gel | |
|---|---|
| Compound of Example 5 | 2.5 g |
| 2-Ethylhexyl p-methoxycinnamate | 2.5 g |
| Cacao butter | 5 g |
| Antioxidants | 0.05 g |
| Silica | 10 g |
| Perfume | 0.5 g |
| Triglycerides q.s.p. | 100 g |

This fatty gel is prepared by heating the fatty substances to about 40°–45° C. and then adding the silica, with vigorous stirring, and the filters.

The same results are obtained by replacing the compound of Example 5 by the compound of Example 3.

EXAMPLE 33

| Sun milk | |
|---|---|
| Compound of Example 2 | 3 g |
| Compound of Example 14 | 2 g |
| Cetyl-stearyl alcohol | 2 g |
| Cetyl alcohol | 2 g |
| Triglycerides of $C_8$ to $C_{12}$ fatty acids | 20 g |
| Lanoline | 4 g |
| Stearic acid | 0.5 g |
| Preservatives | 0.3 g |
| Carbopol 934 (crosslinked polyacrylic acid sold by GOODRICH CHEMICAL) | 0.15 g |
| Triethanolamine | 0.2 g |
| Demineralised water q.s.p. | 100 g |

This emulsion is prepared as in Example 25; the compound of Example 2 is dissolved in the aqueous phase, the compound of Example 14 being dissolved in the fatty phase.

EXAMPLE 34

| Aqueous-alcoholic sun gel | |
|---|---|
| Carbopol 934 | 0.7 g |
| Triethanolamine | 0.35 g |
| Propylene glycol | 25 g |
| 96° strength ethanol | 25 g |
| Compound of Example 2 | 1 g |
| Diethanolamine salt of p-methoxycinnamic acid | 2.5 g |
| Preservative | 0.3 g |
| Perfume | 0.4 g |
| Demineralised water q.s.p. | 100 g |

The carbopol is dispersed in the water with vigorous stirring and the triethanolamine is then added, followed by the solvents and the water, in which the filters have been dissolved beforehand.

The same results are obtained by replacing the compound of Example 2 by the compound of Example 4 in the form of the triethanolamine salt.

EXAMPLE 35

| Sun cream | |
|---|---|
| Compound of Example 7 | 4 g |
| 4-[(2-Oxo-3-bornylidene)-methyl]-phenyl-trimethylammonium methylsulphate | 3.5 g |
| Polyoxyethyleneated fatty alcohols | 7 g |
| Triglycerides of $C_8$ to $C_{12}$ fatty acids | 30 g |
| Glycerol monostearate | 2 g |
| Silicone oil | 1.5 g |
| Cetyl alcohol | 1.5 g |
| Preservatives, perfume q.s. | |
| Demineralised water q.s.p. | 100 g |

The preparation of this cream is similar to that of Example 24, the 4-[(2-oxo-3-bornylidene)-methyl]-phenyltrimethylammonium methylsulphate being dissolved in the water.

The compound of Example 7 can be replaced by 2 g of the compound of Example 12.

EXAMPLE 36

| Sun cream | |
|---|---|
| Compound of Example 14 | 2 g |
| 4'-Methoxy-4-tert.-butyldibenzoylmethane sold under the name PARSOL 1789 by GIVAUDAN | 1 g |
| Polyoxyethyleneated fatty alcohols | 7 g |
| Triglycerides of $C_8$ to $C_{12}$ fatty acids | 30 g |
| Glycerol monostearate | 2 g |
| Silicone oil | 1.5 g |
| Cetyl alcohol | 1.5 g |
| Preservatives | 0.4 g |
| Perfume | 0.5 g |
| Demineralised water q.s.p. | 100 g |

The compound of Example 14 and the Parsol 1789 are dissolved in the fatty phase.

EXAMPLES 37 to 39

In these examples, the compounds of the formula (I) are used to protect coloured compositions from the sun.

EXAMPLE 37

| Coloured Shampoo | |
|---|---|
| Triethanolamine Lauryl-sulphate | 10 g |
| 0.05% strength solution of Orasol Blue BLW | 1 cc |
| Compound of Example 2 | 0.5 g |
| Perfume, preservative q.s. | |
| Water q.s.p. | 100 g |

EXAMPLE 38

| Coloured shampoo | |
|---|---|
| Triethanolamine Lauryl-sulphate | 10 g |
| Compound of Example 1 | 0.8 g |
| Fast Lilac W 5001 (Colour Index No. 45190) | 0.015 g |
| Perfume, preservative q.s. | |
| Water q.s.p. | 100 g |

EXAMPLE 39

| Coloured setting lotion | |
|---|---|
| Polyvinylpyrrolidone copolymer (of average molecular weight 40,000, sold under the code K30 by GAF) | 2 g |
| Fast Red CR1 W 3000 (Colour Index No. 27290) | 0.02 g |
| Compound of Example 3 | 0.3 g |
| 96° strength ethanol | 60 g |
| Water q.s.p. | 100 g |

These compositions do not change colour, even after exposure to the sun for several weeks.

EXAMPLE 40

Sun oil

The following ingredients are mixed, if necessary with heating to 40°–45° C. to homogenise them:

| Sun oil The following ingredients are mixed, if necessary with heating to 40–45° C. to homogenise them: | |
|---|---|
| Compound of Example 15 | 3 g |
| Octyl p-dimethylaminobenzoate | 3 g |
| Cacao butter | 2.5 g |
| Antioxidants | 0.05 g |
| Perfume | 0.5 g |
| Triglycerides of $C_8$ to $C_{12}$ fatty acids q.s.p. | 100 g |

EXAMPLE 41

| Aqueous-alcoholic sun gel | |
|---|---|
| Carbopol 934 | 0.7 g |
| Triethanolamine | 0.35 g |
| Propylene glycol | 25 g |
| 96° strength ethanol | 25 g |
| Compound of Example 16 | 3 g |
| Preservative | 0.3 g |
| Perfume | 0.4 g |
| Demineralised water q.s.p. | 100 g |

The carbopol is dispersed in the water with vigorous stirring and the triethanolamine is then added, followed by the solvents and the water, in which the filter has been dissolved beforehand.

EXAMPLE 42

| Sun cream | |
|---|---|
| Compound of Example 18 | 2.5 g |
| Benzylidene-camphor | 4 g |
| Triglycerides of $C_8$ to $C_{12}$ fatty acids | 31 g |
| Glycerol monostearate | 6 g |
| Stearic acid | 2 g |
| Cetyl alcohol | 1.2 g |
| Lanoline | 4 g |
| Preservatives | 0.3 g |
| Propanediol | 2 g |
| Triethanolamine | 0.5 g |
| Perfume | 0.4 g |
| Demineralised water q.s.p. | 100 g |

The filters are dissolved in the fatty phase.

EXAMPLE 43

| Sun milk | |
|---|---|
| Compound of Example 21 | 3 g |
| Benzylidene-camphor | 2 g |
| Cetyl-stearyl alcohol | 2 g |
| Cetyl alcohol | 2 g |
| Triglycerides of $C_8$ to $C_{12}$ fatty acids | 20 g |
| Lanoline | 4 g |
| Stearic acid | 0.5 g |
| Preservatives | 0.3 g |
| Carbopol 934 (crosslinked polyacrylic acid sold by GOODRICH CHEMICAL) | 0.15 g |
| Triethanolamine | 0.2 g |
| Demineralised water q.s.p. | 100 g |

This emulsion is prepared as in Example 33; the compound of Example 21 is dissolved in the aqueous phase, the benzylidene-camphor being dissolved in the fatty phase.

EXAMPLE 44

| Moisturising face cream | |
|---|---|
| Tween 60 = sorbitan monostearate oxyethyleneated with 20 mols of ethylene oxide, sold by ATLAS | 1 g |
| Cetyl alcohol | 1 g |
| Perhydrosqualene | 10 g |
| Virgin sesame oil | 5 g |
| Stearic acid | 2 g |
| Glycerol | 3 g |
| Compound of Example 20 | 1 g |
| Methyl para-hydroxybenzoate | 0.3 g |
| Perfume | 0.3 g |
| Water q.s.p. | 100 g |

EXAMPLE 45

| Protecting and moisturising fluid body emulsion | |
|---|---|
| Myrj 49 = polyethylene glycol stearate sold by ATLAS | 0.8 g |
| Self-emulsifiable glycerol stearate | 1.2 g |
| Stearyl alcohol | 1 g |
| Vaseline oil | 8 g |
| Soya oil | 3 g |
| Amerchol L 101 = extract of sterols and complex higher alcohols of lanoline, in their free form, sold by AMERCHOL | 3 g |
| Compound of Example 20 | 1.5 g |
| Methyl para-hydroxybenzoate | 0.3 g |
| Perfume | 0.3 g |
| Water q.s.p. | 100 g |

EXAMPLE 46

| Moisturising hand cream | |
|---|---|
| Brij 56 = cetyl alcohol oxyethyleneated with 10 mols of ethylene oxide, sold by ATLAS | 2 g |
| Self-emulsifiable glycerol stearate | 2 g |
| Cetyl alcohol | 1 g |
| Vaseline oil | 5 g |
| Isopropyl myristate | 5 g |
| Lanoline | 3 g |
| Compound of Example 20 | 2 g |
| Methyl para-hydroxybenzoate | 0.3 g |
| Perfume | 0.3 g |
| Water q.s.p. | 100 g |

EXAMPLE 47

| Stimulating cream | |
|---|---|
| Germal 115 = imidazoline/urea copolymer sold by SUTTON LARS | 0.3 g |
| Compound of Example 20 | 1 g |
| Omadine MDS = 2,2'-bis-N—hydroxypyridyl disulphide/magnesium sulphate complex sold by OLIN | 0.025 g |
| Triethanolamine | 0.5 g |
| Cetiol LC = cetyl laurate sold by HENKEL | 1 g |
| Rutile titanium oxide | 0.5 g |
| Triple pressed stearine | 3 g |
| Mixture of glycerol monostearate and distearate | 3 g |
| Double-distilled pure cetyl alcohol | 3 g |
| Nesatol = triglycerides of $C_{10}$–$C_{18}$ fatty acids, sold by VEVY | 1 g |
| Calophyllum oil | 0.5 g |
| BHA = butylhydroxyanisole | 0.03 g |
| Nipa ester 82121 = mixture of methyl, ethyl, propyl, butyl and benzyl para-hydroxybenzoates | 0.2 g |
| Talc | 3 g |
| Octyl p-dimethylaminobenzoate | 1.5 g |
| Perfume | 0.4 g |
| Demineralised water q.s.p. | 100 g |

EXAMPLE 48

| Sun oil | |
|---|---|
| Compound of Example 22 | 1.5 g |
| Compound of Example 23 | 1.5 g |
| Cacao butter | 2.5 g |
| Antioxidants | 0.05 g |
| Perfume | 0.5 g |
| Triglycerides of $C_8$–$C_{12}$ fatty acids q.s.p. | 100 g |

We claim:

1. 3-Benzylidene-camphor derivative having the general formula:

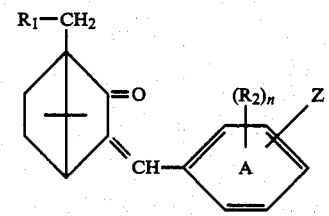

(I)

in which $R_1$ denotes the radical $SO_3^\ominus M^\oplus$, in which M is hydrogen, an alkali metal or the group $N^\oplus(R_3)_4$, each $R_3$ independently denoting hydrogen or a $C_1$ to $C_4$ alkyl or hydroxyalkyl group; $R_2$ denotes a linear or branched $C_1$ to $C_4$ alkyl radical or a $C_1$ to $C_4$ alkoxy radical, n being O or an integer from 1 to 4 such that when n is 2 or more the $R_2$ radicals can be the same or different; and Z represents a group of the formula:

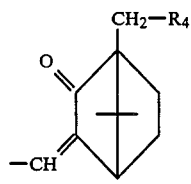

in which $R_4$ is as defined under $R_1$, with the proviso that the methylidene-camphor radical and the radical Z, which are attached to the aromatic nucleus A, are either in the meta position or in the para position relative to one another.

2. A derivative according to claim 1 which has the formula

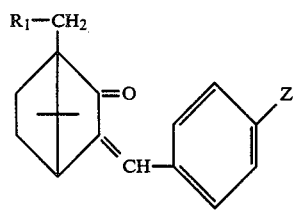 (II)

in which $R_1$ denotes a group—$SO_3H$ and Z denotes a group

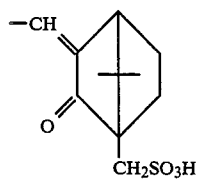

in the form of the free diacid or the sodium or triethanolamine disulphonate.

3. Process for the preparation of a compound as claimed in claim 1 in which Z represents a group:

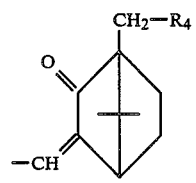

which comprises reacting by heating under reflux a compound of the formula

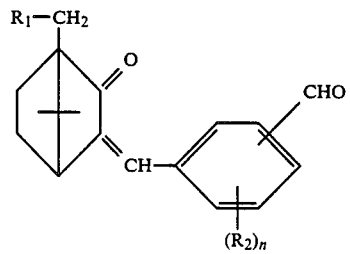

in which $R_2$ is as defined in claim 1, with a compound of the formula:

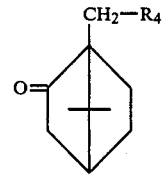

in either anhydrous solvent, in the presence of an organic or inorganic base, the water formed being removed, or alternatively, in a water-immiscible solvent, in the presence of an aqueous solution of sodium hydroxide or potassium hydroxide.

4. Process for the preparation of a compound as claimed in claim 1 in which Z represents a group:

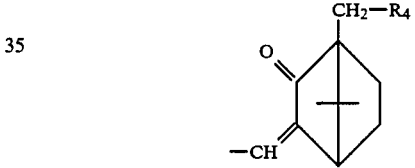

which comprises reacting by heating under reflux one mol of a compound of the formula:

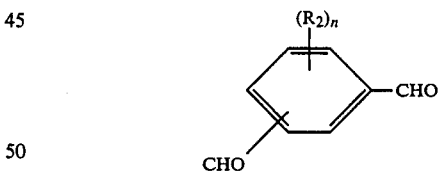

in which $R_2$ is as defined in claim 1, with two mols of a compound of the formula:

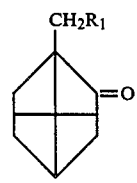

in either an anhydrous solvent, in the presence of an organic or inorganic base, the water formed being removed, or, alternatively, in a water-immiscible solvent, in the presence of an aqueous solution of sodium hydroxide or potassium hydroxide.

5. A composition suitable for cosmetic use which contains at least one 3-benzylidene-camphor derivative as defined in claim 1.

6. A composition which contains at least one derivative as claimed in claim 2.

7. A composition according to claim 5, in which the derivative is present in an amount from 0.5 to 15% by weight, relative to the total weight of the composition.

8. A composition according to claim 5, which contains at least one cosmetic adjuvant which is a thickener, softener, superfatting agent, emollient, humectant, wetting agent, surface-active agent, preservative, antifoam agent, perfume, oil, wax, dyestuff or pigment.

9. A composition according to claim 5, which is in the form of an anti-sunburn composition and contains at least one derivative as claimed in claim 1 associated with another water-soluble or liposoluble sun filter having a filtering action with respect to UV-B rays, or with another sun filter which filters out the UV-A rays.

10. A composition according to claim 9 in which the said sun filter having a filtering action with respect to UV-B rays is a camphor derivative, coffee bean oil, salicylic acid derivative, cinnamic acid derivative, p-aminobenzoic acid derivative or benzophenone derivative.

11. A composition according to claim 9 in which the said sun filter which filters out UV-A rays is a dibenzoylmethane derivative.

12. A composition according to claim 5, which is in the form of a coloured or non-coloured cosmetic composition stabilised to light and is a hair lacquer, a setting lotion, a shampoo, a colouring shampoo or a hair dyeing composition, a nail varnish, a lipstick, an epidermis treatment cream or a make-up foundation.

13. Process for protecting the human epidermis against UV-A and/or UV-B rays, which comprises applying thereto at least one derivative as defined in claim 1.

14. Process for protecting a coloured cosmetic composition against UV radiation, which comprises incorporating therein at least one derivative as defined in claim 1.

* * * * *

UNITED STATES PATENT AND TRADEMARK OFFICE
CERTIFICATE OF CORRECTION

PATENT NO. : 4,585,597
DATED : April 29, 1986
INVENTOR(S) : Gerard LANG et al.

It is certified that error appears in the above-identified patent and that said Letters Patent is hereby corrected as shown below:

Column 7, Example 5, that portion of the formula reading

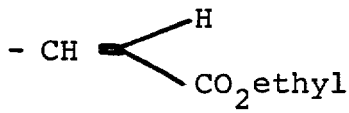

should read

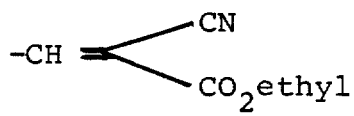

Signed and Sealed this

Twenty-second Day of December, 1987

Attest:

DONALD J. QUIGG

*Attesting Officer*       *Commissioner of Patents and Trademarks*

UNITED STATES PATENT AND TRADEMARK OFFICE

In re L'Oreal S.A.  : CERTIFICATE OF
Request for Patent Term Extension : INTERIM EXTENSION
U.S. Patent No. 4,585,597 :

On May 30, 2003, patent owner L'Oreal S.A. timely filed an application under 35 U.S.C. § 156(d)(5) for an interim extension of the term of U.S. Patent No. 4,585,597. The patent claims the active ingredient (Mexoryl® SX (ecamsule)) in the product ANTHÉLIOS® SP Topical Cream (HELIOBLOCK® SX Cream), and the methods of use and manufacturing of the active ingredient. The application indicates that a New Drug Application for the human drug product ecamsule has been filed and is currently undergoing regulatory review before the Food and Drug Administration for permission to market or use the product commercially.

Review of the application indicates that except for permission to market or use the product commercially, the subject patent would be eligible for an extension of the patent term under 35 U.S.C. § 156. Since it is apparent that the regulatory review period will continue beyond the original expiration date of the patent (June 16, 2003), interim extension of the patent term under 35 U.S.C. § 156(d)(5) is appropriate.

An interim extension under 35 U.S.C. § 156(d)(5) of the term of U.S. Patent No. 4,585,597 is granted for a period of one year from the original expiration date of the patent, i.e., from June 16, 2003, until June 16, 2004.

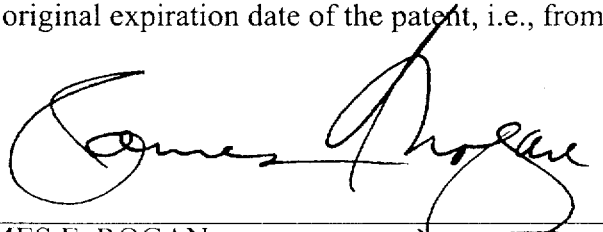

JUN 1 3 2003
_____  _____
Date                         JAMES E. ROGAN
                             Under Secretary of Commerce for Intellectual Property and
                             Director of the United States Patent and Trademark Office